United States Patent [19]
Voss et al.

[11] Patent Number: 5,773,675
[45] Date of Patent: Jun. 30, 1998

[54] METHOD FOR ELIMINATING CARBON OXIDES IN THE HYDROGEN FEED TO A BUTANE ISOMERIZATION PROCESS

[75] Inventors: Andrew P. Voss, Cerritos; Michael J. Pedersen, Irvine, both of Calif.

[73] Assignee: Atlantic Richfield Company, Los Angeles, Calif.

[21] Appl. No.: 732,828

[22] Filed: Oct. 15, 1996

[51] Int. Cl.$^6$ .............................. C07C 1/00; C07C 5/10; C07C 5/13

[52] U.S. Cl. ..................... 585/304; 585/266; 585/734; 423/658.3

[58] Field of Search ................................. 585/304, 266, 585/734; 423/658.3

[56] References Cited

PUBLICATIONS

R. Kramer, M. Fishbacher and H. L. Gruber, "Slow Uptake of Oxygen and Carbon Monoxide bghy Platinum/Silica (Europt–1)and Subsequent Effects on Hydrogenation of Benzene and Hydrogenolysis of Methycyclopentane", *Applied Catalysis*, 42(1988)337–350, Elsevier Science Publishers B.V., Amsterdam—Printed in the Netherlands.
Geltramini, "Catalytic Naphtha Reforming", edited by G.J. Antos, et al; 1995, Mar., Dekket, Inc., pp. 314–315.
Rylander, Paul Nels, Catalytic Hydrogenation over Platinum Metals, New York, Academic Press, 1967, p. 20.
"IFP Process Literature" (Sales Material generally available to Refiners).
"Setting the Pace with IFP for the 21st Century", Jun. 1994 (Promotional Literature from IFP that is generally available to refiners).
Schmidt, R.J., Weiszmann, J.A., and Johnson, J.A., "Catalysts—key to low–cost isomerization", Oil & Gas Journal, May 27, 1985, pp. 80–88.
Schmidt, R.J., Johnson, J.A., Hibbs, F.M. and Froggatt, M.D., "Two New Catalysts for Isomerization of Light Straight Run Naphtha", For Presentation at the Fourth Scientific Conference, Scientific Research Council, Baghdad, Iraq, Oct. 23–28, 1986.
Johnson, J.A., Hobbs, S.H., Wheeler, T., "UOP PENEX Technology—A Flexible Solution", May 5, 1986.
"Section 11 Isomerization", *Modern Refinery Operations & Practices*, Hydrocarbon Publishing Co., 1993, pp. 94–97.
Reno, M.E., Haizmann, R.S., Johnson, B.H., Kuchar, P.J., Piotrowski, P.P. and Zarchy, A.S., Improved Profits with Paraffin Isomerization Innovations, 1990 UOP, Des Plaines, Illinois.

(List continued on next page.)

*Primary Examiner*—Walter D. Griffin
*Assistant Examiner*—In Suk Bullock
*Attorney, Agent, or Firm*—F. Lindsey Scott

[57] ABSTRACT

A method for isomerizing at least a portion of a butane stream using a hydrogen stream containing more than 0.1 ppmv of carbon monoxide, carbon dioxide or a mixture thereof, the method comprising: charging the hydrogen stream containing at least 0.1 ppmv of at least one carbon oxide to a aromatics saturation zone to produce a reduced carbon oxide content hydrogen stream; recovering the reduced carbon oxide content hydrogen stream; drying at least a portion of the reduced carbon oxide content hydrogen stream to produce a dried reduced carbon oxide content hydrogen stream; charging at least a portion of the dried reduced carbon oxide content hydrogen stream to a butane isomerization zone; charging the butane stream to the butane isomerization zone; and, isomerizing at least a portion of the butane to produce an isobutane stream.

11 Claims, 3 Drawing Sheets

PUBLICATIONS

Symoniak, M.F. and Holcombe, T.C., "Total Isomerization Gains Flexibility", *Hydrocarbon Processing*, May 1983, pp. 62–64.

"Isomerization", *Hydrocarbon Processing*, Nov. 1990, p. 122.

*Chemical and Process Technology Encyclopedia*, Douglas M. Considine, Editor, McGraw–Hill Book Co., 1974, pp. 662–665.

Schmidt, R.J. and Weiszmann, J.A., "Low Cost Options for Upgrading Light Straight Run Naphtha", American Petroleum Institute, 1985, 30 pp.

"Applications for Isomerization Processes", ICI PURASPEC Processes, ICI Katalco, Two TransAm Plaza Drive, Oakbrook Terrace, Illinois 60181, 1993, 6 pp.

Lietz, G., and Volter, J., Catalytic Hydrogenation of Methylbenzenes on Platinum, Symposium on the Mechanisms of Hydrocarbon Reactions 5–7 Jun., 1973, Siofok, Hungary, pp. 151–161.

Hibbs, F.M., "New Technologies for Efficient Refining inthe Environmentally Conscious 1990s", Petroleum Review, May 1994, pp. 210–213.

U.S. Patent Application, Voss, Andrew P. et al, "A Method for Eliminating Carbon Oxides in Feeds to a Paraffin Isomerization Process", filed Oct. 16, 1996. (Serial No. 08/732,823).

METHOD FOR ELIMINATING CARBON OXIDES IN THE HYDROGEN FEED TO A BUTANE ISOMERIZATION PROCESS

BACKGROUND OF THE INVENTION

1. Field of the Invention

This invention relates to a method for reducing the benzene content and isomerizing a butane stream using a hydrogen stream containing at least one carbon oxide.

2. Description of Related Art

In refinery processes it is desirable that a substantial portion of the crude oil or other petroleum feed stock to the refinery be converted to gasoline range materials. Gasoline comprises a hydrocarbon fraction generally having a boiling range of about 30° to about 430° F. and a research octane number (RON) of at least about 90. A variety of refinery processes are used to increase the gasoline yield from crude oil charged to a refinery. Such processes include catalytic cracking, reforming, alkylation and the like. In the refining process naphthenic and paraffinic hydrocarbons are produced which are of a suitable boiling range for use as gasoline but which have an octane rating too low for use as gasoline. The octane rating of such hydrocarbons is typically increased by reforming. In the reforming process, the naphthene hydrocarbons and paraffin hydrocarbons are converted to aromatic hydrocarbons. As is well known to those skilled in the art, aromatic materials have a higher octane rating than similar boiling range paraffinic or naphthenic materials.

While such reforming processes are effective to produce higher octane rating materials, the materials so produced are aromatic and in recent years there have been requirements to reduce the aromatic component content of gasoline. While reforming remains a valuable tool for increasing the octane rating of paraffinic hydrocarbons increased attention has been directed to other methods for increasing the octane rating of paraffinic hydrocarbons.

One such method is the use of isomerization. Isomerization of gasoline range paraffins is frequently used with paraffinic hydrocarbons which comprise primarily paraffinic hydrocarbons containing from 5 to 6 carbon atoms. Such $C_5/C_6$ streams are frequently subjected to benzene saturation and isomerization treatment to saturate benzene and convert straight chain hydrocarbons to branched chain, or isomerized. $C_5$ and $C_6$ paraffins which have a higher octane rating than the corresponding straight chain paraffins.

Such isomerization processes are well known to those skilled in the art as discussed in *Chemical and Process Technology Encyclopedia*, Douglas M. Considine, Ed., McGraw Hill Book Company. 1974, pp. 662–665. As discussed in this reference it is a common practice to also isomerize $C_4$ hydrocarbons for use in alkylation processes and the like. It is also noted that moisture must be minimized in the isomerization zone and that the amount of benzene in the paraffin feed stock should be minimized. It is also known to those skilled in the art that carbon oxides, even in small amounts, in the feed stream are extremely detrimental to the isomerization catalyst. Such carbon oxides are methanated over the isomerization catalyst. The methanation reaction produces water which permanently poisons the isomerization catalyst. Accordingly it has long been recognized that carbon oxides in the feed to the isomerization reactor must be minimized and desirably maintained at levels below 0.1 part per million by volume (ppmv).

It has also been recognized that the presence of benzene in the paraffin feed to the isomerization reactor is detrimental since the benzene is hydrogenated over the isomerization catalyst causing an increase in reactor temperature which promotes unwanted cracking reactions and increased hydrogen consumption. Quantities of benzene are commonly present in $C_5$ and $C_6$ paraffin streams which are isomerized for use as gasoline blending components. It is desirable to remove benzene from the $C_5/C_6$ paraffins before the isomerization reaction zone in a unit such as a benzene hydrogenation reactor.

Benzene saturation units have long been known to those skilled in the art and are used to saturate benzene compounds in $C_5/C_6$ paraffinic streams. Such processes typically use a catalyst comprising from about 0.1 to about 1.0 weight percent platinum on a suitable catalyst support such as alumina or silica alumina. Such units typically operate at an inlet temperature from about 325° to 800° F. and a pressure from about 200 to 700 pounds per square inch gauge (psig). Since carbon oxides also temporarily poison the catalyst in the benzene saturation reactor, it has been considered necessary to maintain the carbon oxide content of the streams charged to the benzene saturation reactor at low levels.

In recent years there has been increased interest in removing benzene components from $C_5/C_6$ paraffinic streams and isomerizing $C_5/C_6$ paraffinic streams because of the increased emphasis on the production of gasoline having a reduced aromatics content.

Alkylation is another refinery process which produces a high octane paraffinic gasoline blending stock. Isobutane is a feedstream to alkylation processes and is typically produced by isomerization of normal butane (butane). The isomerization of butane is carried out in isomerization reactors using similar catalysts and reaction conditions to those used to isomerize $C_5/C_6$ paraffins. Unlike the $C_5/C_6$ paraffin streams which commonly contain quantities of benzene because of the similar boiling ranges, the butane feed to the isomerization process rarely contains benzene and is not treated in a benzene saturation reactor to saturate benzene. The $C_5/C_6$ paraffins and butane are normally isomerized in separate isomerization reactors so that the process in each reactor can be optimized to produce the desired product, i.e. isobutane or isomerized $C_5/C_6$ paraffins.

In many refineries the available hydrogen sources contain amounts of carbon monoxide, carbon dioxide or mixtures thereof up to as much as about 100 ppmv. Accordingly, it the past such hydrogen streams have been passed through a methanation reactor to react the carbon oxides to produce water and methane with the resulting water being removed prior to charging the hydrogen to isomerization reactors. Similarly, the carbon oxides have been removed prior to using such hydrogen streams in benzene saturation reactors.

Accordingly, an improved method is desired for reducing the capital cost of butane isomerization processes and effectively using hydrogen streams containing carbon oxides in such isomerization processes.

SUMMARY OF THE INVENTION

The method of the present invention permits the use of a refinery hydrogen stream containing at least one carbon oxide selected from the group consisting of carbon monoxide and carbon dioxide in processes for reducing the benzene content and isomerizing at least a portion of a butane stream, the method comprising:

a) charging the hydrogen stream to an aromatics saturation zone to remove carbon oxides from the hydrogen stream to produce a reduced carbon oxide content hydrogen stream;

b) recovering the reduced carbon oxide content hydrogen stream;

c) drying at least a portion of the reduced carbon oxide content hydrogen stream to produce a dried reduced carbon oxide content hydrogen stream;

d) charging at least a portion of the dried reduced carbon oxide content hydrogen stream and a butane stream to a butane isomerization zone; and e) isomerizing at least a portion of the butane stream in the isomerization zone at a temperature from about 250° to about 600° F., and a pressure from about 100 to about 600 psig in the presence of an isomerization catalyst to produce an isomerized butane stream.

DESCRIPTION OF THE PREFERRED EMBODIMENTS

In the description of the Figures, the same numbers will be used throughout to refer to the same or similar components. Various pumps, valves and the like necessary to achieve the indicated flows have not been shown except when necessary for the process flow description.

Figure 1:
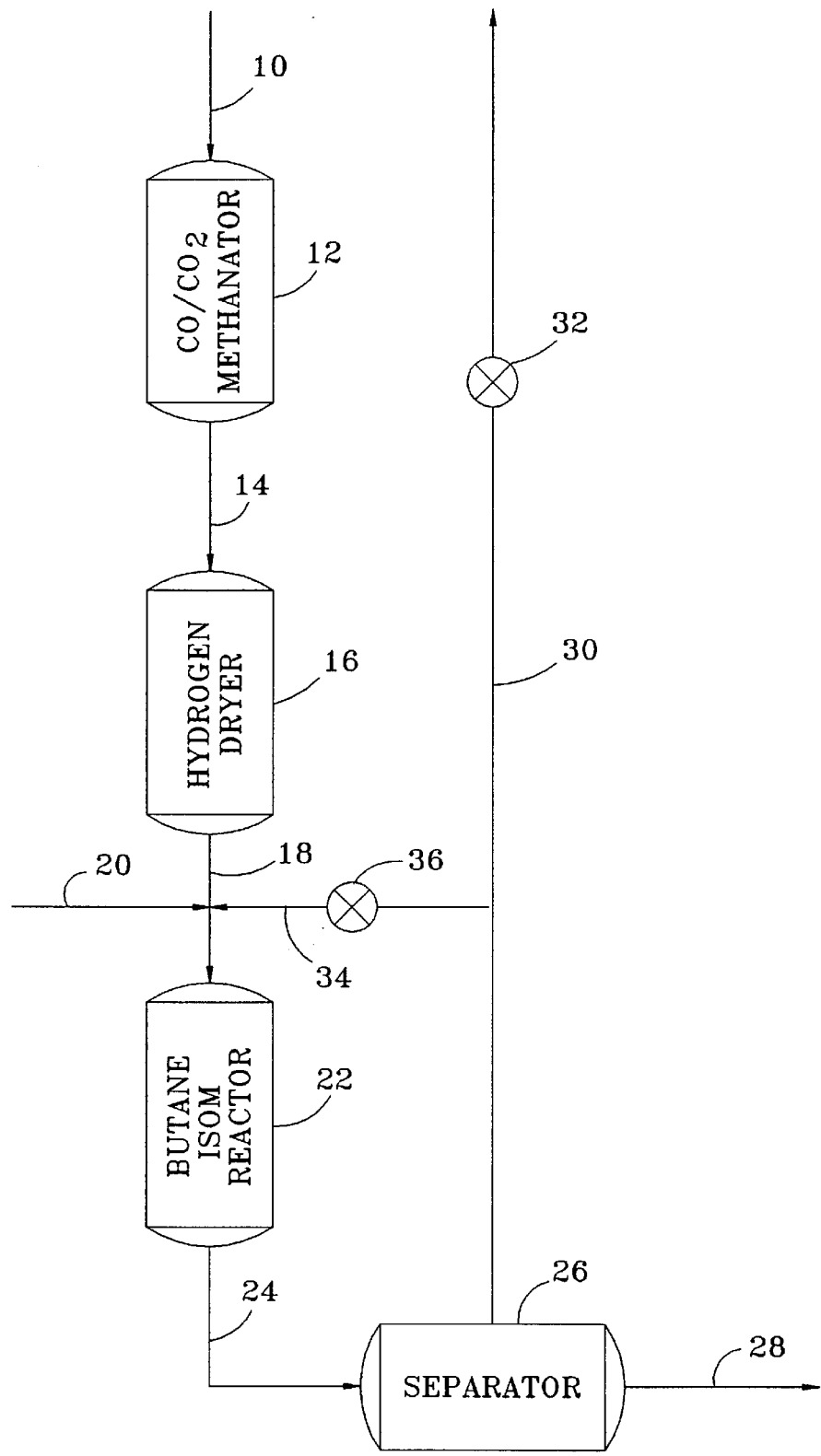
FIG. 1 is a schematic diagram of a prior art process wherein a butane stream is isomerized using a hydrogen stream containing carbon oxides to produce an isobutane stream.

In FIG. 1 a hydrogen line 10 supplies hydrogen containing more than 0.1 ppmv of carbon monoxide, carbon dioxide or mixtures thereof to a $CO/CO_2$ methanator 12 containing a suitable methanation catalyst which is typically a nickel-based catalyst. Methanation catalysts are considered to be well known to those skilled in the art as are methanation conditions. The resulting methanated stream containing hydrogen, methane and water passes through a line 14 to a hydrogen dryer 16 where water is removed. Hydrogen dryer 16 may be any suitable hydrogen drying system. The dried hydrogen then passes through a line 18 to a butane isomerization reactor 22. A butane feed stream which is preferably at least 50 percent butane, is fed through a line 20 and combined with the hydrogen in line 18 for charging to butane isomerization reactor 22. The reaction product comprising isobutane is recovered through a line 24 and passed to a separator 26 where hydrogen is recovered through a line 30 and passed to discharge from the process through line 30 or recycled at least in part to butane isomerization reactor 22 through a line 34. The flows through lines 30 and 34 are controlled by a valve 32 in line 30 and a valve 36 in line 34. While a portion of the hydrogen may be recycled to reactor 22, the hydrogen will contain methane from $CO/CO_2$ methanator 12 and other light gases. These gases must be periodically removed from the process when they reach unacceptable levels. The operation of such butane isomerization processes is considered to be well known to those skilled in the art.

The use of the $CO/CO_2$ methanator is necessary to remove carbon oxides from the hydrogen stream required in butane isomerization reactor 22. As discussed in *Chemical and Process Technology Encyclopedia*, page 665, moisture is the most important impurity to minimize in the isomerization process. Carbon oxides methanate readily over the isomerization catalyst to produce water which is a poison to the isomerization catalyst. Accordingly when hydrogen containing quantities of carbon oxides is used to isomerize butane it is necessary to remove the carbon oxides prior to charging the hydrogen to the isomerization reactor.

Figure 2:
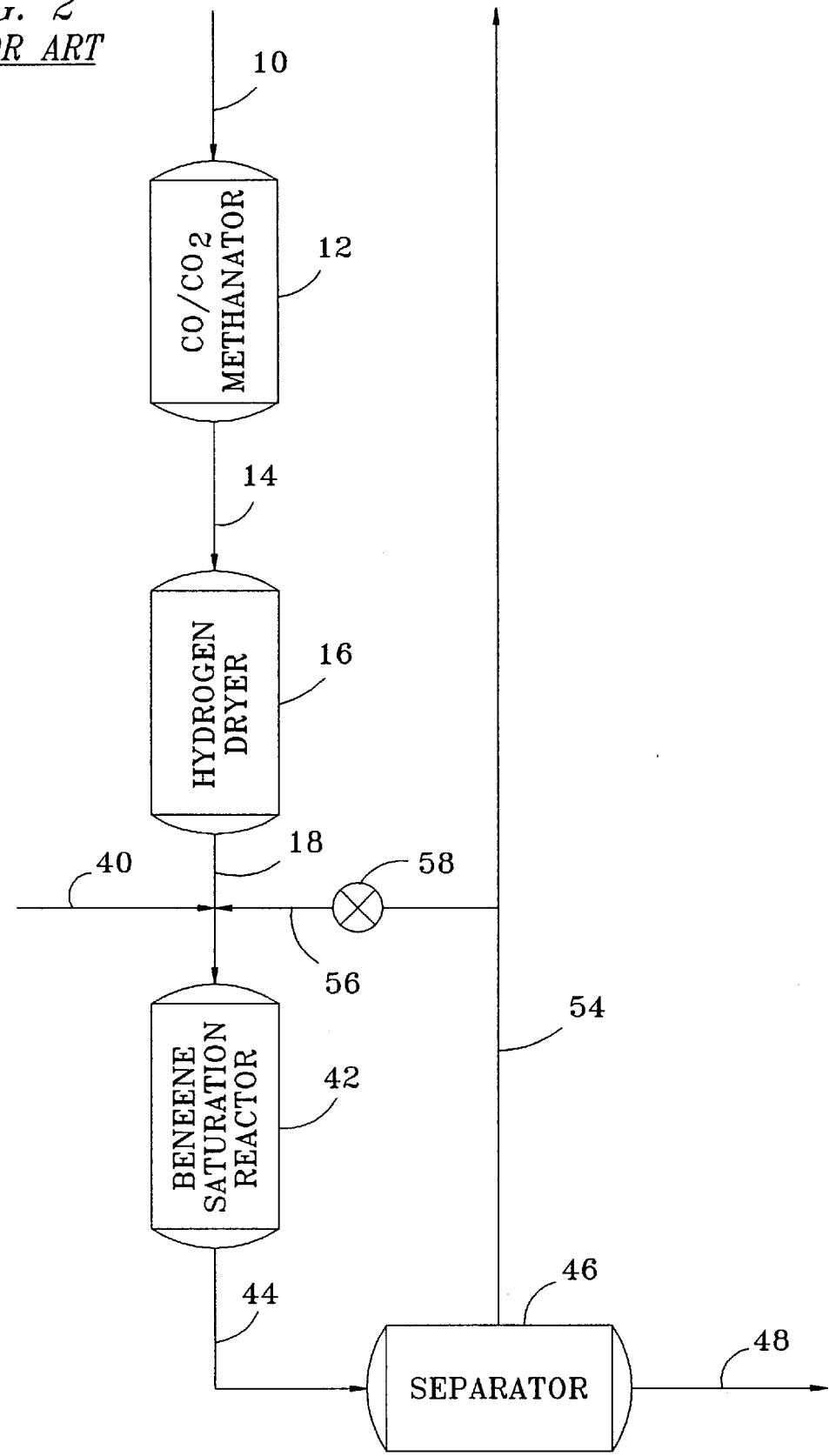
FIG. 2 is a schematic diagram of a prior art benzene saturation process.

In FIG. 2 a prior art aromatic saturation process is shown. A benzene saturation process is shown as an example of aromatic saturation processes using a precious metal catalyst. A hydrogen stream containing carbon oxides is charged through a line 10 to a $CO/CO_2$ methanator 12 wherein the carbon oxides are converted to methane and water with the resulting stream being passed through a line 14 to a hydrogen dryer 16. The dried hydrogen is passed through a line 18 to a benzene saturation reactor 42 in combination with a liquid hydrocarbon stream supplied through a line 40. The liquid hydrocarbon stream supplied through line 40 is typically a mixture of $C_5$ and $C_6$ paraffins. Frequently, quantities of benzene are found in such streams as a result of the refinery processes which produce the streams. This is primarily a result of the close boiling ranges of some of the $C_5$ and $C_6$ paraffins and the benzene. The combined streams are charged to a benzene saturation reactor 42 where the benzene is saturated with the product stream then being recovered through a line 44 and passed to a separator 46. In separator 46 the liquid hydrocarbons are recovered through a line 48 and may be passed to use as a feedstock to a $C_5/C_6$ paraffin isomerization reaction process, sold as a solvent, or some similar application. The hydrogen is recovered through a line 54 and may be discharged from the process or recycled to benzene saturation reactor 42 through a line 56 and a valve 58. Such processes are considered to be well known to those skilled in the art.

When $C_5$ and $C_6$ paraffins are isomerized to produce isomerized paraffins for use as gasoline components and the like, the $C_5$ and $C_6$ paraffin stream is frequently passed through a benzene saturation reactor prior to the isomerization reactor to saturate benzene since the presence of the benzene in the isomerization reactor is undesirable.

In the process shown in FIG. 2 a $CO/CO_2$ methanator and a hydrogen dryer are used to treat the hydrogen charged to benzene saturation reactor 42. In "Slow Uptake of Oxygen and Carbon Monoxide by Platinum/Silica (EUROPT-1) and Subsequent Effects on Hydrogenation of Benzene and Hydrogenolysis of Metholcyclepentane" R. Kramer, M. Fischbacher and H. L. Gruber, Applied Catalysis, 42 (1988) 337–350 it is disclosed that when sufficient amounts of carbon monoxide is added to the reaction mixture charged to a benzene saturation process the activity of the catalyst is greatly reduced and when sufficient carbon monoxide is present in the catalyst substantially no catalytic activity is observed. Accordingly, it has been considered by those skilled in the art that carbon oxides must be removed to a very low level from streams charged to a benzene saturation reactor.

The operation of benzene saturation processes as described above is considered to be well known to those skilled in the art. In the benzene saturation reactor a catalyst comprising about 0.1 to about 1.0 weight percent platinum alumina, alumina silicate or the like may be used as a catalyst at a temperature typically from about 325° to about 800° F. and a pressure typically from about 200 to about 700 psig. The paraffin stream velocity in the benzene saturation reactor is typically from about 2 to about 10 liquid hourly space velocity (LHSV). LHSV is defined as the volume of liquid feed per unit volume of catalyst per hour. The operating temperature is limited by the upper operating temperature limits of the catalyst and reactor and may limit the amount of benzene which may be included in the charge to the reactor. The operating temperature is also limited by the chemical equilibrium of the benzene hydrogenation reaction which is not favorable above about 800° F. Such processes are widely used with $C_5$ and $C_6$ paraffin streams which are to be isomerized to produce isomerized $C_5$ and $C_6$ paraffin streams. Other hydrocarbon streams may also be treated using similar catalysts to hydrogenate aromatic compounds.

Suitable isomerization catalysts for such isomerization reactions include supported platinum group metal catalysts which may comprise from about 0.1 to about 2.0 weight percent platinum group metal components supported on activated alumina, crystalline aluminosilicate or other suitable support materials. The catalyst may also contain rhodium group metal components as well as promoters. Such catalysts may also contain up to 20 weight percent acidic chloride components and are generally considered to be highly acidic catalysts. Such catalysts are considered to be known to those skilled in the art.

The mixture of hydrogen and feed stock is typically charged to the $C_5$ and $C_6$ isomerization reactor at a temperature from about 250° to about 600° F. and a pressure of about 100 to about 600 psig. The hydrogen is desirably supplied to such isomerization processes in an amount equal to from about 500 to about 4000 standard cubic feet per barrel of $C_5/C_6$ paraffin feedstock. The LHSV in such isomerization reactors is typically from about 1 to about 4.

Butane is typically isomerized using similar catalysts and similar reaction conditions although butane is not normally isomerized in the same reaction vessel. Separate isomerization processes are used because it is desirable to optimize the yield of isobutane in the butane isomerization process and it is desirable to optimize the yield of isomerized $C_5$ and $C_6$ paraffins in the $C_5/C_6$ paraffin isomerization process. Further, butane rarely contains significant quantities of benzene as produced in a refinery because of the wide difference in the boiling points of butane and benzene. Accordingly, butane isomerization processes do not include a benzene saturation reactor.

It has now been discovered by applicants that aromatics saturation reactors such as benzene saturation reactors, can tolerate substantial quantities i.e. up to at least about 100 ppmv of carbon monoxide, carbon dioxide or mixtures thereof in a hydrogen stream without inhibiting the aromatic saturation catalyst to the extent that the aromatic saturation reaction is adversely affected. It is preferred that the carbon oxide content be less than about 10.0 ppmv and desirably less than about 5.0 ppmv. Benzene saturation reactors as discussed herein are representative of such aromatics saturation reactors.

While carbon oxides are known to temporarily poison and inhibit the functioning of aromatic saturation catalysts, it has been found that this damage is not significant when less than about 100 ppmv of carbon oxides are present in the hydrogen charged to the aromatics saturation reactor.

Figure 3:
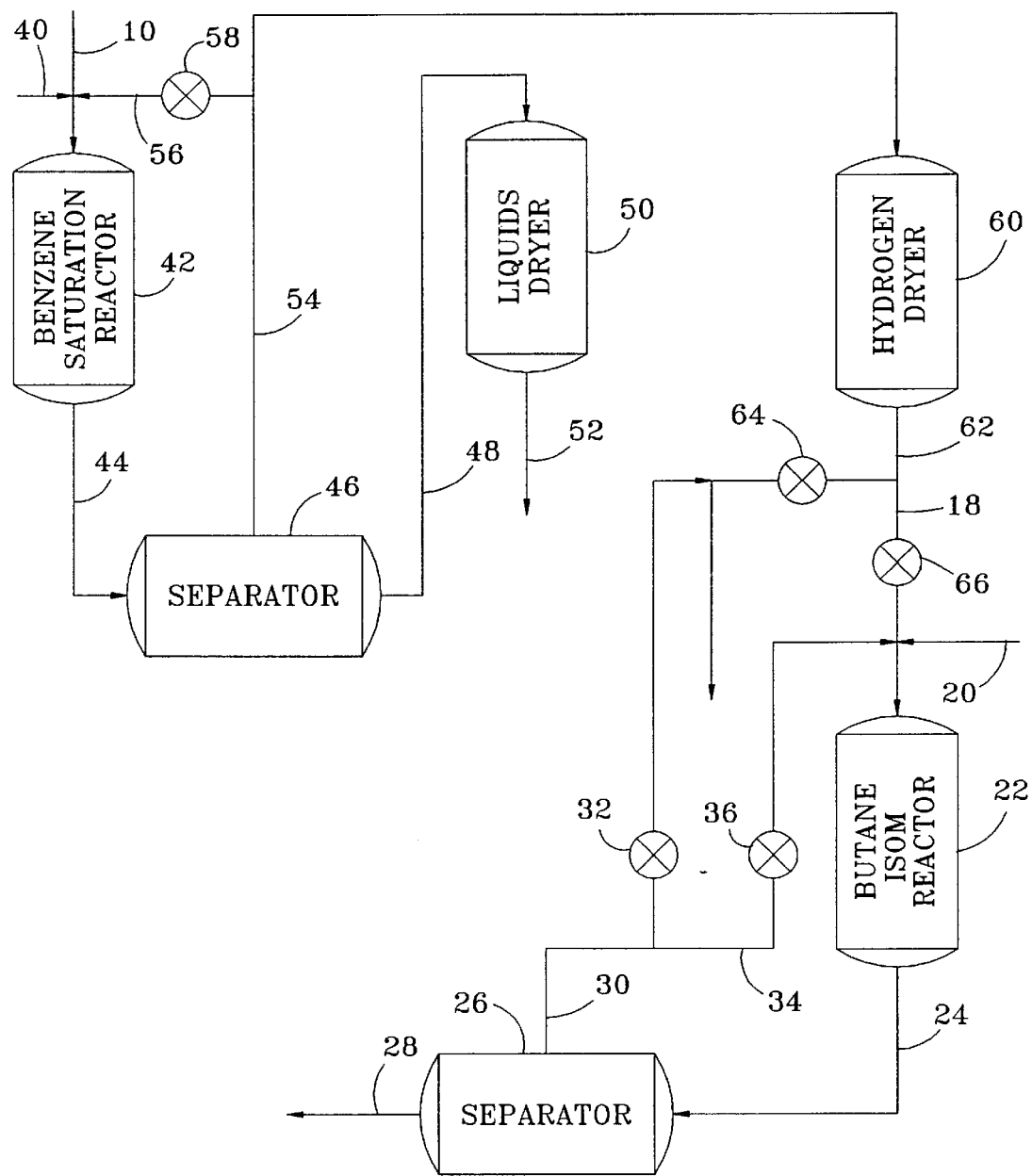
FIG. 3 is a schematic diagram of an embodiment of the method of the present invention.

In FIG. 3 a hydrogen stream 10 containing up to 100 ppmv of carbon monoxide, carbon dioxide or a mixture thereof is charged to a benzene saturation reactor 42 in combination with a liquid hydrocarbon stream charged through a line 40. The liquid hydrocarbon stream comprises $C_5$ and $C_6$ paraffins containing quantities of benzene. The benzene is saturated in benzene saturation reactor 42 and a $C_5/C_6$ paraffin stream having a reduced benzene content is recovered through a line 44 and passed to a separator 46. In separator 46 the $C_5/C_6$ paraffin stream is recovered through a line 48 and passed through a liquids dryer if the $C_5$ and $C_6$ paraffins are to be isomerized or the like. The dried liquid hydrocarbon stream is recovered through a line 52 and passed to further processing product sales or the like. A reduced carbon oxide content hydrogen stream is recovered from separator 46 through a line 54 and passed to a hydrogen dryer 60. A stream of hydrogen may be recycled to benzene saturation reactor 42 through a line 56 and a valve 58 if desired.

Hydrogen dryer 60 may be any suitable hydrogen dryer. The dried hydrogen stream is recovered through a line 62 and passed through a valve 64 to use in other processes such as a $C_5$ and $C_6$ paraffin isomerization reactor or the like. A stream of the dried hydrogen is withdrawn through a line 18 and passed through a valve 66 to a butane isomerization reactor 22. Butane is passed to butane isomerization reactor 22 through a line 20 and an isobutane product stream is recovered through a line 24. The recovered isobutane stream is passed to a separator 26 where isobutane is recovered through a line 28 and a hydrogen stream is recovered through a line 30 and passed through a valve 32 to combination with the hydrogen from line 62 or optionally passed through a line 34 and a valve 36 back to butane isomerization reactor 22.

By the process of the present invention, as discussed above, the butane isomerization process can be operated using hydrogen containing carbon monoxide, carbon dioxide and mixtures thereof without a $CO_5/CO_6$ methanator.

As discussed previously the use of a benzene saturation reactor in combination with $C_5$ and $C_6$ paraffin isomerization processes is well known and is frequently used to produce $C_5$ and $C_6$ isoparaffin blending stocks. Such processes provide carbon oxide free dried hydrogen for use in the $C_5/C_6$ isomerization process. The use of this benzene saturation reactor to remove carbon oxides from hydrogen for the butane isomerization process eliminates the need for a carbon oxide methanator and a hydrogen dryer in connection with the butane isomerization process. The elimination of the hydrogen dryer is a result of excess capacity in the hydrogen dryer required for use in the $C_5/C_6$ paraffin isomerization process.

A $C_5/C_6$ paraffin isomerization process utilizing carbon oxide containing hydrogen as a feed stock to a $CO_5/CO_6$ paraffin isomerization process is disclosed in co-pending application U.S. Ser. No. 08/732,823 entitled "A Method For Eliminating Carbon Oxides in Feeds to a $C_5$ and $C_6$ Paraffin Isomerization Process" by Andrew P. Voss and Michael J. Pedersen filed of even date herewith.

The butane isomerization reactor uses a similar type catalyst as the $C_5/C_6$ paraffin isomerization reactor. Accordingly the sensitivity of the butane isomerization catalyst to water and carbon oxides is an equally important consideration in the butane isomerization process.

By the process of the present invention sufficient hydrogen is charged to benzene saturation reactor 42 so that sufficient hydrogen is available to flow through benzene saturation reactor 42 to butane isomerization reactor 22. The carbon oxides are thus removed in the benzene saturation reactor with no detriment to the benzene saturation process and without the need for a methanation vessel in either process. Similarly, the use of a single hydrogen dryer may be sufficient for both the butane isomerization process and the $C_5/C_6$ paraffin isomerization process. This is a significant process simplification and results in significant capital and operating cost savings in the butane isomerization process. The butane may be dried prior to charging it to the butane isomerization zone if necessary.

In many instances the hydrogen available in refinery operations contains small amounts of carbon oxides. Such carbon oxides can be detrimental to the benzene saturation catalyst at high concentrations because of competitive adsorption. They are particularly detrimental and result in permanent deactivation of the isomerization reactor catalyst because of water produced from the methanation reaction. It is very desirable that such streams be available for use in benzene saturation and in isomerization processes because hydrogen free of carbon oxides is not always available.

According to the present invention such streams are readily used in benzene saturation and in butane isomerization processes with no detriment to either process. While the carbon oxides tend to temporarily deactivate the benzene saturation catalyst to a slight extent the deactivation is insufficient to inhibit the function of the catalyst for benzene saturation. Since the deactivation is temporary the slight amount of deactivation caused by the presence of carbon oxides in the hydrogen charged to the benzene saturation reactor does not result in sufficient cumulative detriment to the benzene saturation catalyst to prevent the effective saturation of benzene. The resulting hydrogen stream is then dried to remove the water and used in the isomerization reactor to isomerize the butane stream. The process of the present invention has thus resulted in the use of a hydrogen stream which has been produced in a benzene saturation reactor as part of a different process to remove undesirable carbon oxides at a point in the process where their removal is not detrimental to the function of the benzene saturation reactor or the $C_5/C_6$ paraffin isomerization process to produce carbon oxide free hydrogen required for use in the butane isomerization reactor. The process of the present invention eliminates the need for a separate methanation reactor and a dryer for the butane isomerization process.

Having thus described the present invention by reference to certain of its preferred embodiments it is pointed out that the embodiments described are illustrative rather than limiting in nature and that many variations and modifications are possible within the scope of the present invention. Such variations and modifications may be considered obvious and desirable by those skilled in the art based upon the foregoing description of preferred embodiments.

Having thus described the invention we claim:

1. A method for isomerizing at least a portion of a butane stream using a hydrogen stream containing at least one carbon oxide selected from the group consisting of carbon monoxide and carbon dioxide, the method comprising;
    a) charging the hydrogen stream to an aromatics saturation reactor to remove carbon oxides from the hydrogen stream to produce a reduced carbon oxide content hydrogen stream;
    b) recovering at least a portion of the reduced carbon oxide content hydrogen stream;
    c) drying at least a portion of the reduced carbon oxide content hydrogen stream;
    d) charging the reduced carbon oxide hydrogen stream and a butane stream to an isomerization zone; and
    e) isomerizing at least a portion of the butane stream in the isomerization zone at a temperature from about 250° to about 600° F. and a pressure from about 100 to about 600 psig in the presence of an isomerization catalyst to produce an isobutane stream.

2. The method of claim 1 wherein the hydrogen stream contains more than about 5.0 ppmv of at least one carbon oxide.

3. The method claim 1 wherein the hydrogen stream contains more than about 10.0 ppmv of at least one carbon oxide.

4. The method of claim 1 wherein the hydrogen stream contains from about 5.0 to about 100.0 ppmv of at least one carbon oxide.

5. The method of claim 1 wherein the aromatics saturation catalyst comprises from about 0.1 to about 1.0 weight percent platinum supported on alumina.

6. The method of claim 1 wherein the reduced carbon oxide content hydrogen stream contains less than about 0.1 ppmv carbon oxide.

7. The method of claim 1 wherein the isomerization catalyst comprises an acidic catalyst comprising from about 0.1 to about 2.0 weight percent platinum group metal component supported on a suitable support and up to about 20 weight percent acidic chloride components and wherein the isomerization zone is at a temperature from about 275° to about 350° F. and a pressure from about 100 to about 500 psig.

8. The method of claim 1 wherein the liquid hourly space velocity of the butane stream in the isomerization reactor is from about 1 to about 4.

9. The method of claim 1 wherein at least a portion of the butane stream is dried prior to charging to the isomerization zone.

10. The method of claim 1 wherein the hydrogen is present in the isomerization zone in an amount equal to from about 500 to about 4000 standard cubic feet per barrel of butane.

11. The method of claim 1 wherein the aromatics saturation reactor is a benzene saturation reactor.

* * * * *